United States Patent [19]

Chan et al.

[11] Patent Number: 4,975,092
[45] Date of Patent: Dec. 4, 1990

[54] PROCESSES FOR COLORING AND/OR CONDITIONING HAIR

[75] Inventors: Alexander C. Chan, Mineola, N.Y.; Yuh-Guo Pan; Leszek J. Wolfram, both of Stamford, Conn.

[73] Assignee: Clairol Incorporated, New York City, N.Y.

[21] Appl. No.: 438,139

[22] Filed: Nov. 16, 1989

Related U.S. Application Data

[63] Continuation-in-part of Ser. No. 193,971, May 13, 1988, abandoned.

[51] Int. Cl.$^5$ .............................................. A61K 7/13
[52] U.S. Cl. .......................................... 8/408; 8/407; 8/416; 8/410
[58] Field of Search ................... 8/416, 407, 408, 410, 8/411, 421, 424; 564/305

[56] References Cited

U.S. PATENT DOCUMENTS

| | | | |
|---|---|---|---|
| 4,008,043 | 2/1977 | Kalopissis et al. | 8/408 |
| 4,725,283 | 2/1988 | Cotteret et al. | 8/407 |

*Primary Examiner*—Paul Lieberman
*Assistant Examiner*—John F. McNally
*Attorney, Agent, or Firm*—S. Nolan

[57] ABSTRACT

A process for coloring and/or conditioning hair using modified primary intermediates and/or a modified coupler containing a hydrophobic group or a group containing a cationic site amenable to reaction with an anionic surfactant; novel modified primary intermediates and modified couplers also being disclosed as well as novel synthetic methods for making these compounds.

10 Claims, No Drawings

PROCESSES FOR COLORING AND/OR CONDITIONING HAIR

This application is a continuation-in-part of application Ser. No. 07/193,971, filed May 13, 1988 and now abandoned.

BACKGROUND

The invention relates to a process for coloring and/or conditioning hair, especially on the human head, and to compositions that are useful in this process. It also concerns certain novel compounds that may be employed in such process and compositions and a process for preparing these compounds.

Oxidative hair coloring (tinting) is known to result frequently in deterioration of hair fiber combability and feel. These changes in hair properties are readily perceptible by the consumer who is likely to interpret them in terms of hair "damage". The precise reason for these undesirable changes is unclear. While the oxidation of the hair surface (by peroxide present in the color formulation) may play a part, it appears that the more likely culprit is the deposition of dye moieties on such surface. There is a progressive deterioration in combability and feel of the hair with the increased intensity of dye-outs (i.e. the darker shades are more deleterious in this respect than the lighter ones although the peroxide concentration in all shades is identical).

Currently, the only way to deal with this problem is to mask the effect by application of conditioning agents. The use of conventional conditioners either during or after the hair coloring process leaves the hair easy to comb and with a pleasant feel, but both of these conditioning attributes disappear after a single shampoo. Cationic polymer conditioning products are somewhat more durable in this respect but even they lose their effectiveness in several shampoos.

INVENTION

It has now been unexpectedly discovered, in light of what is generally believed, that hair may be colored and/or conditioned to improve, for example, its feel or combability by subjecting the hair to treatment under oxidative conditions with a composition containing a modified precursor selected from the group consisting of a modified primary intermediate, a modified coupler and mixtures thereof. The modified primary intermediates and the modified couplers are characterized by the fact that they contain organic groups which serve to render oxidative reaction products of said modified primary intermediates or modified couplers more suitable for conditioning hair or serve to render such reaction products more amendable to reaction with anionic hair conditioning agents to condition hair. Organic groups or the first type will generally be long chain aliphatic hydrophobic groups. Organic groups of the second type will usually not be hydrophobic in character but will contain a cationic site that may bind to an anionic hair conditioning agent.

The precise mechanism by which the process of the present invention operates is not fully understood. However, it is believed that, in the case where the modified precursors contain long chain aliphatic hydrophobic groups, the products formed in the oxidative reactions become attached to the cuticular surface of the hair and, due to the presence of the long chain hydrophobic groups, provide a relatively permanent lubricating effect resulting in ease of combing and soft feel.

In the case where the modified precursor does not contain the long chain hydrophobic group but does contain a cationic site, the oxidative reaction product of such modified precursor also binds to the cuticular surface. This provides a cationic site on the cuticle that is amenable to reaction with an anionic hair conditioning agent.

DESCRIPTION OF THE INVENTION

Unless stated otherwise, all disclosures cited are hereby incorporated by reference.

As used herein the term "primary intermediate containing a long chain hydrophobic group" refers to primary intermediates well known in the hair dye art which have been modified by the introduction into its structure of at least one long chain hydrophobic group. Primary intermediates in the hair dye art are characterized by the fact that they develop color under oxidizing conditions. Similarly, the term "coupler containing a long chain hydrophobic group" refers to couplers also well known in the hair dye art which have been modified by the introduction of long chain hydrophobic groups. The couplers are characterized by the fact that while they do not produce color in themselves they will modify the color of the primary intermediates under oxidative conditions. (See article entitled "Hair Coloring" by John F. Corbett and John Menkart in *Custis*, Vol. 12, August 1973, pages 192 and 193).

The term "modified primary intermediate" is used herein to refer to primary intermediates that have been modified by introducing into the primary intermediate a hydrophobic group or non-hydrophobic group that contains a cationic site. It also extends to those cases wherein the hydrophobic group on the primary intermediate also contains a cationic site. Similarly, the term "modified coupler" is used herein to refer to couplers that have been modified by introducing into the coupler a hydrophobic group or a non-hydrophobic group that contains a cationic site. In a similar fashion the term "modified coupler" also encompasses those couplers containing both a hydrophobic and a cationic site.

Although the primary intermediates and the couplers employed herein are color developing compounds under oxidative conditions, it is not essential to the present process that a significant coloring is obtained on the hair. Thus, a conditioning effect may sometimes be obtained without color development when the quantities of primary intermediates and couplers contained in the treating compositions are not sufficient to produce significant coloring.

As used herein the term "long chain hydrophobic group" refers to a long chain radical that imparts hydrophobic characteristics to the primary intermediate or coupler compound to which it is attached. The long chain radicals will generally be aliphatic radicals containing from about 8 to about 32 atoms which will consists primarily of carbon atoms but may contain other atoms in the chain (e.g, O, N, and the like). Such long chain radicals may also have cationic sites as, for example, a quaternary nitrogen site and, in addition to the principal chain of 8 to 32 atoms, have side chains which, when present, will ordinarily be alkyl, hydroxyalkyl, or alkoxyalkyl groups whose alkyl moieties contain from about 1 to about 4 carbon atoms.

The term "organic group which is amenable to reaction with an anionic conditioning agent" as used herein refers to an organic group which, it itself, when attached to a primary intermediate or a coupler is not capable of rendering the oxidative reaction product hydrophobic. These will usually be short chain aliphatic groups containing from about 3 to about 7 atoms in the chain which contain a cationic site (e.g. quaternary nitrogen) capable of binding with an anionic detergent. These short chain aliphatic groups may likewise contain branch chain groups which will ordinarily be alkyl, hydroxyalkyl or alkoxyalkyl groups in which the alkyl moieties contain 1 to 4 carbon atoms.

The modified primary intermediates that are useful in practicing the process of the present invention may be more specifically defined by the formula

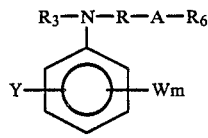

(I)

wherein:
(a) A is a divalent radical selected from the group consisting of $CH_2$ and the group

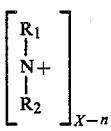

in which $R_1$ and $R_2$ are each independently alkyl, hydroxyalkyl, and alkoxyalkyl whose alkyl moieties contain 1 to 4 carbon atoms and in which $X^{-n}$, wherein $n=1$, 2, or 3 is an anion;

(b) R is a divalent alkylene group having 1-6 carbon atoms.

(c) Y is ortho or para to the substituted amino group and is selected from the group consisting of

and OH;

(d) $R_3$, $R_4$ and $R_5$ are each independently selected from each other and are selected from the group consisting of hydrogen, alkyl, hydroxyalkyl, and alkoxyalkyl whose alkyl moieties contain 1 to 4 carbon atoms;

(e) $R_6$ is an alkyl group consisting 1 to 24 carbon atoms;

(f) W is selected from the group consisting of hydrogen, alkyl, hydroxyalkyl and halogen, wherein the alkyl groups contain 1 to 6 contain atoms, and (g) $m=1$ to 4.

While $R_6$ can contain from about 1 to about 24 carbon atoms, it is preferred that it contain from 1 to 18 carbon atoms, with groups containing 1 to 6 or 12 to 18 being highly preferred.

A number of categories of preferred modified primary intermediates useful herein are given in formulas II to V below. When $R_3$, $R_4$ or $R_5$ are present in these formulas they are the same or different and have the same values ascribed to them above in connection with formula I. $R_7$ in these formulas is an alkyl radical containing 8 to 24 carbon atoms and preferably 12 to 18 carbon atoms, e.g., dodecyl, hexadecyl, octadecyl, etc.

II

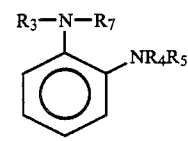

III

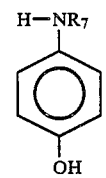

IV

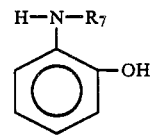

V

Another category of modified primary intermediates are defined by formula VI below; in this case the aliphatic chain contains a cationic center of the general formula:

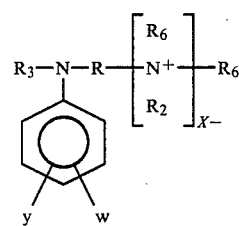

VI wherein
Y is ortho or para to the substituted amino group and is selected from the group consisting of OH, and

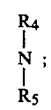

and
R, $R_1$, $R_2$, $R_3$, $R_4$, $R_5$, $R_6$, W, and X have the same value ascribed to them in connection with the formula I.

In this case optionally, $R_6$ is an alkyl radical containing 12 to 18 carbon atoms e.g. dodecyl, hexadecyl, octadecyl, etc. Likewise, in the more preferred case Y occupies a position that is ortho or para to the amine group.

Exemplary of the anions that are represented by $X^{-n}$, wherein $n-1$, 2, or 3, mention may be made of the halides, e.g. ($Cl^-$, $Br^-$, $I^-$), the sulfates (i.e. $SO_4^{-2}$), the phosphates (i.e. $PO_4^{-3}$) tetrafluoro-borate ($BF_4^-$ hydroxide (OH−), etc. When n is 2 or 3, the number of cationic moieties will be greater.

Further in illustration of the types of modified primary intermediates containing a cationic site, more generally shown in formula VI the following formulas VII to X are given. In these cases R, $R_1$, $R_2$, $R_3$, $R_4$, $R_5$ and $R_6$ have the same value ascribed to them above in connection with formula VI. In the more preferred instances $R_6$ is an alkyl radical containing 12 to 18 carbon atoms, e.g. dodecyl, hexadecyl, octadecyl and R is the divalent radical ethylene (i.e. $CH_2-CH_2$)

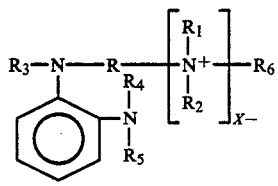

VII

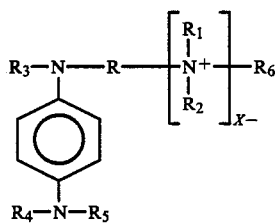

VIII

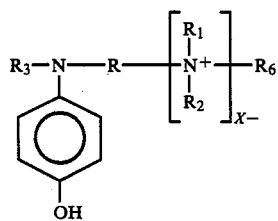

IX

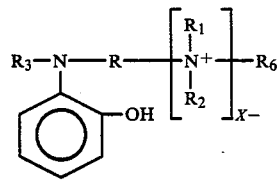

X

The modified primary intermediates of the type defined in formulas VI through X above are more substantive to hair and as a consequence will have, as components of formed dyes, greater resistance to shampooing and will give longer lasting effects.

To illustrate more specifically the modified primary intermediates containing at least one long chain hydrophobic group that may be used in the practice of the present invention mention may be made of the following: N-octadecyl-p-phenylenediamine; 2-(4-aminoanilino)ethyl dimethyloctadecylammonium bromide; 5-amino-2-octadecylaminotoluene; 2-amino-5-octadecylaminotolunene, and the like.

As indicated previously it is also a feature of the present invention to sometimes use as a modified primary intermediate a compound which in itself does not provide hydrophobic or conditioning characteristics to the oxidative reaction product formed in the process of this invention. These primary intermediates, will however, generally contain at least one cationic site which will be formed in the process of this invention. These intermediates will contain cationic sites which will make the reaction products amenable to binding with anionic detergents to provide a conditioning effect.

Illustrative of the primary intermediates of this type are a group of compounds defined by the formula:

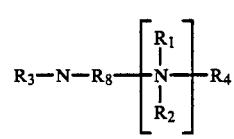

XI wherein $R_8$ is a short chain divalent alkylene radical containing from 2 to 6 carbon atoms;

$R_9$ is a short chain alkyl group containing from 1 to 6 carbon atoms; and $R_1$, $R_2$, $R_3$, $X^{-n}$, wherein n=1, 2, or 3, Y and W have the same meanings ascribed to them in connection with formula I.

The preferred compounds of this group can be described by the formula:

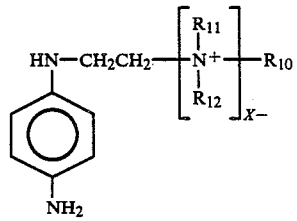

XII in which $R_{11}$ and $R_{12}$ are each independently methyl or ethyl; $X^{-n}$, wherein n=1, 2, or 3, is an anion as described above in connection with formula I; and $R_{10}$ is alkyl having from 1 to 4 carbon atoms.

As also indicated above, in one aspect of this invention a modified coupler will be employed in the practice of the present invention. In this case a conventional coupler will be modified by binding it to a long chain aliphatic hydrophobic group which will provide hair conditioning properties to the oxidation reaction product of those modified couplers.

In an alternative case, the modified coupler will in and of itself not contain a hydrophobic group. However, it will contain a cationic site which will render the oxidative reaction product of these modified couplers amenable to reaction with an anionic conditioning agent for the hair.

The modified couplers that have been found to be most useful in the practice of this invention are the anilino, phenolic or naphtholic couplers that contain long chain aliphatic hydrophobic groups or groups containing a cationic site amenable to reaction with an anionic surfactant. More specifically, the preferred modified couplers can be described by the formulas:

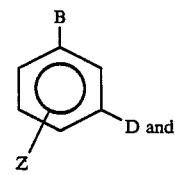

XIII

D and

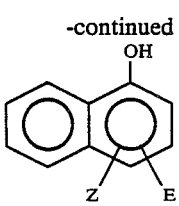

wherein
B is $NHR_{13}$, OH, or $NH_2$;
D is $NHR_{13}$, OH, or $NH_2$;
Z is H, $R_{14}$, or $NHR_{13}$; and
E is H, $NH_2$, $R_{13}$, or $NHR_{14}$; in which
$R_{13}$ is selected from the group consisting of:
(a) long chain alkyl having 7 to 32 carbon atoms, or
(b)

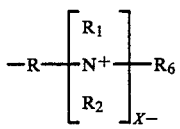

in which
(1) R, $R_1$, $R_2$, $R_6$, and $X^{-n}$, wherein n=1, 2, or 3, have the same meanings ascribed to them in connection with formula I.

and in which $R_{14}$ is a long chain alkyl having from 7 to 32 carbon atoms; at least one of B, D, E or Z being the radical $NHR_{13}$ or $R_{14}$ as defined above. Mixtures are operable.

Among the preferred modified couplers that are useful in the present invention are the compounds of the following formulas:

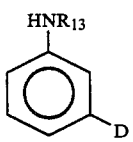

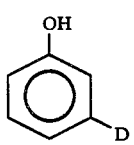

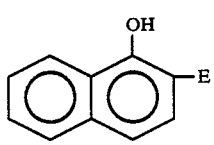

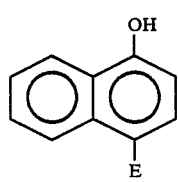

in which D and E have the meanings ascribed to them above in connection with formula XIII and XIV.

To illustrate more specifically the modified couplers that may be used in the practice of the present invention mention may be made of: 4-dodecylresorcinol; 4-dodecylphenol; 4-amino-2-hydroxybenzyldodecyldimethylammonium iodide and the like.

It is a further feature of this invention that the present modified precursors (i.e. modified primary intermediates or modified couplers) may be used in conjunction with one or more conventional oxidative dye precursors (also sometimes referred to herein as conventional precursors) that are reactive with said modified precursors under oxidative conditions to produce color on hair. Thus, for example, when the modified precursor employed is of the primary intermediate type it may be used in conjunction with a conventional coupler. Similarly, when the modified precursor is of the coupler type it may be utilized in conjunction with a conventional primary intermediate.

The rationale for this is to be found in the fact that the oxidative dye precursors which have long alkyl chains as substituents do not, on account of their size, penetrate into the hair quickly enough to be very effective as deep hair colorants. It has been found, however, that when these modified precursors are combined with conventional precursors the resulting formulation provides improved coloring as well as built in conditioning.

In using the process of the present invention, it is contemplated that ordinarily a combination of at least one primary intermediate and at least one coupler will be applied to the hair under oxidative conditions. A variety of combinations of types of primary intermediates and couplers may be used for this purpose. Thus, a modified primary intermediate may be used in conjunction with a conventional coupler and/or a modified coupler. Similarly, a modified coupler may be used in conjunction with a conventional primary intermediate and/or a modified primary intermediate.

It may be the case that the degree of coloration obtained when the only color forming compounds incorporated in the treatment composition are a modified precursor and a conventional precursor, reactive therewith to develop color under oxidative conditions, is not sufficiently deep. This can occur, for example, when a modified primary intermediate is employed along with a conventional coupler or a modified coupler is used along with a conventional primary intermediate. In the former case, a conventional primary intermediate may also be incorporated in the treatment composition. In the latter case, conventional coupler may also be contained in the treatment composition. In each case, sufficient conventional primary intermediate and conventional coupler will be contained in the composition to provide an excess of conventional primary intermediate or conventional coupler over and above that required to react with the modified precursor contained in the composition. That is, stoichiometric excesses are useful.

A wide variety of conventional primary intermediates and conventional couplers may be used in carrying out the process of the present invention. Examples of such conventional primary intermediates include p-phenylenediamine, p-aminophenol, N,N-dimethyl-p-phenylenediamine, N-methyl-p-phenylenediamine, 2,5-diaminotoluene, N,N-bishydroxyethyl-p-phenylenediamine and the like. By way of illustration the conventional couplers that may be employed in the instant invention, mention may be made of the following: resorcinol, 1-naphtol, 5-amine-o-cresol, m-aminophenol, 2-methylresorcinol and like. Mixtures are operable.

As previously noted, it is a feature of the present invention to utilize as a modified primary intermediate or as a modified coupler, compounds which in and of themselves do not contain long chain hydrophobic groups but are capable of binding to anionic detergents. This capability is generally due to the fact that such modified primary intermediates or modified couplers contain a cationic site.

A wide variety of anionic detergents may be used in connection with this aspect of the invention. Examples of such anionic detergents include: salts of oleic acids; salts of lauric acid (e.g., sodium laurate and sodium lauryl sulfate); sulfonate salts (e.g., sodium dodecyl-benezenesulfonate); organic sulfate (e.g., sodium myristyl sulfate) and similar agents. Mixtures can be used.

The compositions of this invention will ordinarily be made up in two or more parts. When two or more parts are employed, considerations such as reagent stability will generally dictate the final make-up of each part. In typical compositions made up of two parts, one part referred to herein as the "concentrate", will usually contain the modified precursor (or precursors) and, where present, the conventional primary intermediate (or intermediates) and/or the conventional coupler (or couplers). The other part, referred to herein as the "developer" contains an oxidizing system and will be described hereinafter in more detail.

The quantity of modified precursor (i.e. modified primary intermediate or modified coupler) that will be contained in the concentrates of this invention may vary depending on the other ingredients in the concentrate as well as the results desired. It is generally required that it be present in sufficient concentration so that when it reacts under oxidizing conditions and is applied to hair, it produces a product that adequately conditions the hair. Although the reaction of a modified precursor of this invention under oxidative conditions may provide some color this is not a major consideration.

In general, the concentrates of the present invention will contain the modified precursors of this invention at a concentration in the range of from about 0.01% to about 3% by weight based on the total weight of the concentrate, the preferred range being from about 0.1% to about 0.5% by weight on the same weight basis.

Unless stated otherwise, all percentages recited herein are weight percentages, based on the total weight of the composition under discussion.

The quantity of conventional precursor, when contained in the concentrates of this invention, will vary depending to a large degree on the other constituents of the concentrate. Where for example, the modified precursor is of the primary intermediate type and is the only primary intermediate in the concentrate, all that is required is that sufficient conventional coupler be present to react with said modified precursor, i.e., equal molar quantities.

Where, however, the concentrate also contains a conventional primary intermediate the quantity of conventional coupler contained in the concentrate will be adjusted so that the coupler is present in sufficient quantity to also react with the conventional primary intermediate to produce a color on the hair. Similar considerations are applicable when the modified precursor is a modified coupler and the conventional precursor is a conventional primary intermediate.

In general terms it may be said that the conventional precursor will be contained in the concentrate at a concentration at least sufficient to react with the modified precursor of this invention which is present in the concentrate.

The concentrates of this invention will usually be in liquid vehicles, in which the various ingredients are dissolved or otherwise distributed. For the most part useful vehicles will be aqueous. However, the vehicle may contain one or more organic solvents that are added for the purpose of solubilizing the dye intermediates that are contained in the concentrate.

By way of illustrating the organic solvents that may be contained in the present concentrates mention may be made of ethanol, isopropanol, glycerine, ethylene glycol, propylene glycol, ethylene glycol monoethyl ester, diethylene glycol, diethylene glycol monoethyl ether.

The concentration of organic solvent may vary over a wide range. Generally, however, it will constitute from about 1% to about 20% by weight, based on the total weight of the concentrate.

As indicated above, a concentrate embodying the present invention may be formed by adding a modified precursor of this invention to a conventional oxidative dye concentrate. Such a concentrate may contain other adjuvants commonly incorporated in such compositions. Thus it may contain other conventional primary intermediates, color couplers, nitro dyes, surfactants, thickening agents, antioxidants, soaps, alkalizing agents, perfumes, EDTA, etc.

The concentrates of this invention will generally have alkaline pH's. Usually, the pH value will be in the range of from about 8 to about 11, with the preferred range being about pH 9 to 10. This, however, does not exclude the possibility of using these compounds under neutral or acidic conditions if special color effects obtained at such pH values are desired.

The various components that may comprise a conventional dye concentrate containing a modified precursor according to this invention are summarized in the following table.

TABLE

| Component | Percentage by wt., % General* | Percentage by wt., % Preferred* |
|---|---|---|
| 1. Modified Precursor | 0.05 to 5 | 0.1 to 0.5 |
| 2. Conventional Primary Intermediate | 0.2 to 5 | 0.1 to 2 |
| 3. Conventional Couplers | 0.1 to 5 | 0.1 to 2 |
| 4. Nitro dyes | 0.01 to 1 | 0.1 to 0.5 |
| 5. Soap | 1 to 20 | 5 to 10 |
| 6. Surfactant | 1 to 20 | 5 to 10 |
| 7. Thickening Agent | 0.5 to 5 | 1 to 3 |
| 8. Antioxidants | 0.01 to 1 | 0.1 to 0.5 |
| 9. Organic Solvents | 3 to 20 | 5 to 10 |
| 10. Water Qs to 100% | 40 to 90 | 60 to 80 |
| 11. Alkalizing Agent to pH | 8 to 11 | 9 to 11 |

The aforesaid concentrates of this invention are intended for use in conjunction with conventional oxidative dye "developers", which contain the oxidizing agent necessary to effect reaction to colored products. Typical developers that are useful for this purpose are aqueous solutions of (a) hydrogen peroxide (e.g. 5 to 12%), (b) high viscosity creams containing in addition to the oxidizing agent, nonylphenol polyethylene glycol or lauryl alcohol polyethylene glycol; (c) crystalline peroxide such as urea peroxide or melamine peroxide.

In use, a volume of the developer described above is mixed with an equal volume of concentrate described previously. Usually, the amount of developer taken is far in excess of that required to oxidize the intermediates, the amounts taken being dependent on the form and concentration of the developer selected. The mixture is well mixed and applied to hair. It can be applied as a shampoo to the entire head or applied to one area of the hair, such as the roots and combed through the rest of the hair later. The mixture is allowed to remain on the head for a period of time and is then removed by shampooing. The normal time of application is 20-30 minutes, but application times of from 10 minutes to one hour can be used.

As noted above, in one aspect of this invention, a modified precursor may be employed which, when applied to hair from compositions containing the same does not condition hair by itself. Such modified precursors are, however, amenable to reaction with an anionic detergent by virtue of the presence of at least one cationic site in their structures. In such cases, the hair, in addition to treatment with a composition containing such a modified precursor is also treated with a composition containing an anionic detergent.

Useful compositions of this type can be exemplified by conventional shampoos based on anionic detergents. Such a shampoo is applied to hair in a conventional manner, worked into a lather and rinsed off. The anionic (i.e. negatively charged) moiety of the detergent molecule is bound to the hair at the cationic site of the grafted dye, while the hydrophobic moiety of the detergent provides smooth feel and silky appearance to the hair.

The modified precursors that are useful for the purposes of the present invention may be prepared by a variety of methods depending on the nature of the compounds. Thus, for example, long chain N-alkylated couplers can be prepared by treating the corresponding anilines with high molecular weight alkyl halides or by reacting anilines and high molecular weight alkyl aldehydes via, e.g., reductive amination techniques. Standard Friedel-Crafts reactions were used to obtain modified couplers containing a long chain alkyl group bonded to a ring carbon atom. Long chain substituted resorcinols and N-substituted aminophenols can be prepared by the acylation of the corresponding aromatic compound followed by reduction of the carbonyl group.

Modified primary intermediates of the p-phenylenediamine type can also be readily prepared. Such processes, as illustrated by the case of p-phenylenediamine, are prepared by reacting fluoronitrobenzene with a long chain alkyl amine. The product of this reaction is reduced under hydrogen atmosphere in the presence of a catalytic amount of 10% Pd/C. The N-long chain alkyl p-phenylenediamine is obtained in the form of its acid salt.

Further aspects of the present invention are the provision of certain novel modified primary intermediates and couplers containing side chains containing quaternary amine sites, that are useful in the composition and processes of this invention, and a novel process for preparing such compounds. The novel primary intermediates may be defined by formulas VI, VII, VIII, IX, X, XI and XII above. Of special interest are the modified p-phenylenediamines that are described by the formula

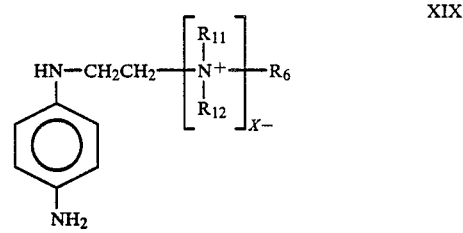

wherein $R_{11}$ and $R_{12}$ are methyl and ethyl and $R_6$ is an alkyl radical containing about 1 to 24, and preferably 1 to 18, carbon atoms, and $X^{-n}$, wherein $n=1, 2,$ or $3$, is an anion, e.g. $Cl^-$, $Br^-$, $I^-$, $SO_4^{-2}$, $PO_4^{-3}$, $OH^-$, $BF_4^-$, etc.

A convenient synthetic route for the preparation of compounds of formula XIX makes use of p-fluoronitrobenzene as a starting material. The latter is reacted with a diamine (e.g. $NH_2-CH_2CH_2-N(CH_3)_2$), to give an N-substituted nitroaniline. This step is followed by quaternization with an alkyl halide.

This general procedure is exemplified in the following equation:

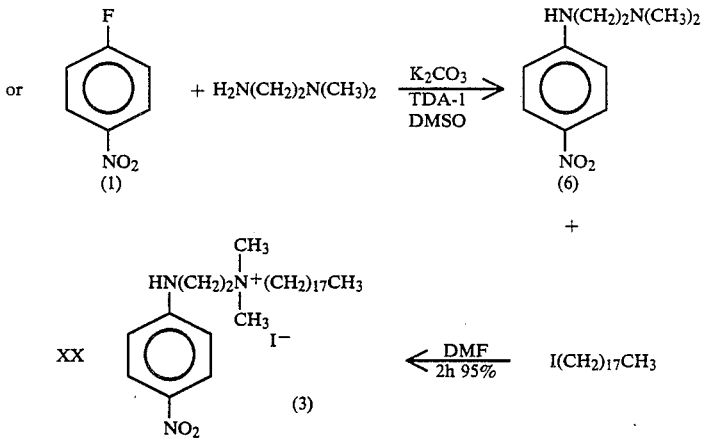

wherein TDA-1 is tris(3,6-dioxaheptyl)amine; DMSO is dimethylsulfoxide and DMF is N,N-dimethylformamide.

To obtain the desired p-phenylenediame type compounds still required the reduction of the nitro group in compound (3) of equation XX. This, however, presented a problem since under ordinary reductive conditions the quaternary salts (e.g. compounds (3)) undergo reductive dealkylation. Several methods were attempted without success. For example, no hydrogen uptake took place by compound (3) over Pd/C catalyst overnight. Reduction attempt with stannous chloride gave only a tarry material.

It was finally discovered, quite unexpectedly, that the necessary selective reduction of compound (3) could be accomplished by hydrogenation over platinum oxide in methanol. This turned out to be a clean and efficient selective reduction and the product was recovered as the halide salt. This reaction can be represented by the following equation.

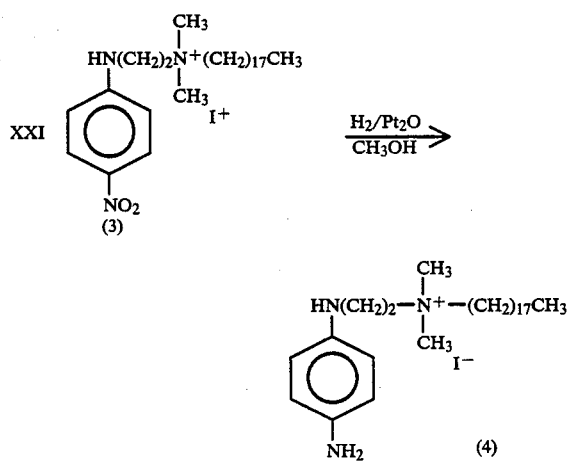

Compound (4) can be recovered from the reaction mixture by mixing it into a suitable acid/alkanol solution, e.g., a solution of hydrochloric acid in methanol. The product is recovered as halide salt(s), probably a mixture of the iodide and chloride salts.

One class of novel modified couplers embraced in the present invention and useful in the compositions and processes employed herein is described by the formula:

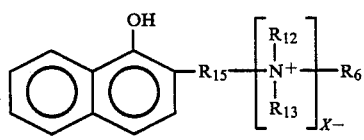

wherein $R_{15}$ is the divalent alkylene radical having 1 to 4 carbon atoms, $R_{12}$ and $R_{13}$ are methyl or ethyl, $R_6$ is an alkyl radical having from 1 to 24 and, preferably from 1 to 18, carbon atoms and $X^{-n}$, wherein $n=1$, 2, or 3, is an anion as defined above.

The preparation of this class of naphthol compounds has been reported in the literature by A. Blodi-Font and T. M. Rocabozera at *J.C.S. Perkin I*, 1982 p. 841.

The following examples further illustrate the present invention.

A. SYNTHETICS EXAMPLES

EXAMPLE 1

(a) Preparation of N-(2-Dimethylaminoethyl)-4-nitroaniline

To a stirred solution of 4-fluoronitrobenzene (7 g, 50 mmol), N,N-dimethylethylenediamine (5.2 g, 60 mmol) and potassium carbonate (7 g, 50 mmol) in 25 ml of dimethysulfoxide was added 0.2 g of tris(3,6-dioxaheptyl) amine(TDA-1). The heterogenous mixture was heated at 90° for 2 h. After cooling to room temperature, 100 g of crushed ice was added to precipitate out the yellow product in 90% yield (9.4 g, 45 mmol).

(b) Quaternization of N-(2-Dimethylaminoethyl)-4-nitroaniline with alkyl halides A solution of 5 mmol of N-(2-dimethylaminoethyl)-4-nitroaniline and 6 mmol of alkyl halide, e.g., 1-octadecyl iodide in 10 ml of N,N-dimethylformamide was heated at 90°. The progress of reaction was followed by chromatography until the disappearance of the starting material. After cooling to room temperature, the quaternary ammonium salt was isolated in 95% yield by filtration following by washing with acetone.

EXAMPLE 2

Preparation of 2-(4-aminoanilino) ethyldimethylalkylammonium iodide chloride

Dimethyl-2-(4-nitroanilino)ethyloctadecylammonium iodide (1.0 g, 1.7 mmol) was hydrogenated at 30 psi in 50 ml of methanol with 0.1 g of PtO₂ at room temperature for 30 min. After removal of the catalyst, 50 ml of saturated methanolic hydrogen chloride was added. The desired product was isolated as its hydrohalide salt in quantitative yield.

EXAMPLE 3

Synthesis of N-octadecyl-p-phenylenediamine p-Fluoronitrobenzene (4.3 g, 30 mmol) was dissolved in 50 ml of ethoxyethanol. Octadecylamine (8.6 g, 32 mmol) and sodium bicarbonate (2.9 g. 35 mmol) were added, and the mixture was heated at reflux overnight. The hot reaction mixture was filtered and water was added to the filtrate to cause precipitation of p-nitro-N-octadecylaniline, which was recrystallized from 95% ethanol twice. The yellow solid (1.0 g, 2.6 mmol) was mixed with 0.1 g of Pd/C (5%) in dry ethanol. The mixture was shaken under hydrogen atmosphere at 45° C. until no hydrogen uptake was observed. The solution was filtered into an acidic ethanolic solution. The phenylenediamine was isolated as its sulfate salt by filtration (yield: 0.77 g, 2.0 mmol; 80%).

EXAMPLE 4

Preparation of 4-dodecylresorcinal

This compound was prepared according to the procedure in the literature (E. Klarmann, *J. Am. Chem. Soc.*, 1926, 48, 2358). Lauric acid was heated with zinc chloride until most of the chloride dissolved. The mixture was cooled slightly before the addition of resorcinol. At the end of the reaction, the hot mixture was poured into hot water with vigorous stirring, and the reaction product, 1,3-dihydroxy-4-laurophenone, was extracted with ether. After the evaporation of the solvent, the keto compound was heated with amalgamated zinc and hydrochloric acid. The final product was extracted with ether and recrystallized from petroleum ether/benzene mixture.

EXAMPLE 5

Preparation of 2-(4-nitroanilino)ethyltrimethylammonium iodide

A solution of N-2-dimethylaminoethyl)-4-nitroaniline (1.1 g, 5.3 mmol) and methyliodide (0.9 g, 6.3 mmol) was stirred in 10 ml of N,N-dimethylformamide at room temperature for 1 hour. After addition of acetone, quaternary ammonium salt was isolated in quantitative yields (1.8 g).

EXAMPLE 6

Preparation of 2-(4-aminoanilino)ethyltrimethylammonium iodide hydrochloride 2-(4-Nitroanilino)ethyltrimethylammonium iodide (1.0 g, 2.8 mmol) was hydrogenated at 30 psi in 50 ml of methanol with 0.1 g of $PtO_2$ at room temperature for 30 min. After removal of the catalyst, 50 ml of saturated methanolic hydrogen chloride was added. The desired product was isolated as its hydrochloride salt in quantitive yield (1.0 g, 2.8 mmol).

EXAMPLE 7

Preparation of N-(3-dimethylaminopropyl)-4-nitroaniline

To a stirred solution of 4-fluoronitrobenzene (7 g, 50 mmol), 3-dimethylaminopropylamine (6.1 g, 60 mmol) and potassium carbonate (7 g, 50 mmol) in 25 ml of dimethylsulfoixde was added 0.2 g of tris(3,6-dioxaheptyl)amine (TDA-1). The heterogenous mixture was heated at 90° for 2 h. After cooling to room temperature, 110 g of crushed ice was added to precipitate out the yellow product in 85% yield (9.5 g, 43 mmol).

EXAMPLE 8

Preparation of 2-(4-nitroanilino)propyltrimethylammonium iodide

A solution of N-(3-dimethylamino-propyl)-4-nitroaniline (1.2 g, 5.5 mmol) and methylioide (0.9 g, 6 mmol) was stirred in 10 ml of N,N-dimethylformamide at room temperature for 1 h. After addition of acetone, quaternary ammonium salt was isolated in 90% yield (1.8 g, 5.0 mmol).

EXAMPLE 9

Preparation of 2-4(aminoanilino)propyltrimethylammonium iodide hydrochloride 2-(4-Nitroanilino)propyltrimethylammonium iodide (1.0 g, 2.7 mmol) was hydrogenated at 30 psi in 50 ml of methanol with 0.1 g of $PtO_2$ at room temperature for 30 min. After removal of the catalyst, 50 ml of methanol saturated with hydrogen chloride was added. The desired product was isolated as its hydrochloride salt in quantitive yield (1.0 g, 2.7 mmol).

Set out below are examples of compositions containing modified primary intermediates and/or modified couplers. The ingredients of each composition are expressed in weight percent.

EXAMPLE 10

A hair coloring composition for dyeing the hair to a light brown shade has been made up of the following ingredients.

| Water | 53.9% |
|---|---|
| Oleic acid | 11% |
| Propylene glycol | 13% |
| Isopropyl alcohol | 5% |
| Octoxynol-1 | 9% |
| Ammonium hydroxide | 3% |
| Cocamide DEA | 2% |
| Sulfated castor oil | 2% |
| p-Aminophenol | 0.4% |
| 1-Naphthol | 0.03% |
| Resorcinol | 0.2% |
| p-Phenylenediamine | 0.1% |
| N-Octadecyl-p-phenylenediamine | 0.15% |
| 4-Amino-2-hydroxytoluene | 0.22 |
| | 100% |

EXAMPLE 11

A hair coloring composition for dyeing the hair to a medium brown shade has been made up of the following ingredients.

| Water | 50.0 |
|---|---|
| Oleic acid | 17.0 |
| Propylene glycol | 14.0 |
| Octoxynol-1 | 6.9 |
| Octoxynol-4 | 3.5 |
| Ammonium hydroxide | 3.0 |
| Ethoxydoglycol | 2.5 |
| Sulfated castor oil | 2.0 |
| p-Phenylenediamine | 0.2 |
| N-Dodecyl-p-phenylenediamine | 0.1 |
| 1-Naphthol | 0.1 |
| N,N-bis(2-Hydroxyethyl) p-phenylenediamine | 0.1 |
| Resorcinol | 0.3 |
| 4-Dodecylresorcinol | 0.3 |
| | 100.0% |

EXAMPLE 12

A hair coloring composition for dyeing the hair to a dark brown shade has been made up of the following ingredients.

| Water | 45.0 |
|---|---|
| Oleic acid | 15.0 |
| Propylene glycol | 10.0 |
| Isopropyl alcohol | 10.0 |
| Octoxynol-1 | 5.0 |
| Monoxynol-4 | 4.0 |
| Ammonium hydroxide | 3.0 |
| Cocamine DEA | 2.0 |
| PEG- 8 Tallow amine | 2.0 |
| Sulfated castor oil | 1.5 |
| Resorcinol | 0.6 |
| 4-Hexadecylresorcinol | 0.2 |
| p-Phenylenediamine | 0.8 |
| 1-Naphthol | 0.1 |
| N,N-bis(2-Hydroxyethyl)-p-Phenylenediamine | 0.3 |
| | 100.0% |

To effect the hair coloring aliquants of each of the compositions described in Example 7 through 9 was mixed prior to application to hair with equal weight aliquants of 6% aqueous solution of $H_2O_2$. The mixture was applied to hair tress with proper care being taken to distribute the mixture well between the fibers of the tress. The tresses were allowed to stand in shallow glass containers for 20 min. at the ambient laboratory conditions (temperature 23° C. and humidity of 52%). After this time, the tresses were rinsed under tap water and evaluated for color and tactile properties. In each case, the desired color was obtained and the tresses felt soft to the touch, and combed easily both wet and dry. These conditioning characteristics of dyed hair—so different from those of typical oxidation dye process—persisted upon repeated shampooing.

Reasonable variations, such as those which would occur to a skilled artisan can be made herein without departing from the scope of the invention.

We claim:

1. In a process for coloring, conditioning or coloring and conditioning hair the improvement which comprises subjecting the hair, under oxidative conditions, to the action of a composition containing at least a first modified primary intermediate which is a compound having the formula:

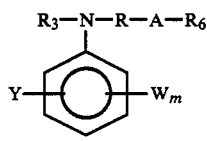

wherein:
(a) A is a divalent radical selected from the group consisting of $CH_2$ and the group

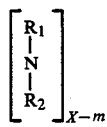

in which $R_1$ and $R_2$ are alkyl, hydroxyalkyl, or alkoxyalkyl, whose alkyl moeities contain 1 to 4 carbon atoms and in which $X^{-n}$ is an anion wherein n=1, 2, or 3;
(b) R is a divalent alkylene group having 1-6 carbon atoms;
(c) Y is selected from the group consisting of

and OH;
(d) $R_3$, $R_4$ and $R_5$ are the same or different and are selected from the group consisting of hydrogen, alkyl, hydroxyalkyl and alkoxyalkyl, in which the alkyl moieties contain 1 to 4 carbon atoms;
(e) $R_6$ is an alkyl group containing 1 to 24 carbon atoms; and
(f) W is selected from the group consisting of hydrogen, alkyl, hydroxyalkyl and halogen wherein the alkyl groups contain 1 to 6 carbon atoms, and
(g) m=1 to 4.

2. The process according to claim 1 wherein said primary intermediate coupler contains a long chain aliphatic hydrophobic group.

3. The process according to claim 1 wherein said primary intermediate contains a short chain aliphatic group containing a cationic center.

4. The process according to claim 3 wherein said hair is also subjected to treatment with an anionic detergent.

5. The process according to claim 1 wherein said long chain aliphatic hydrophobic group contains from 8 to 32 atoms.

6. The process according to claim 1 wherein said primary intermediate contains a cationic center and $R_6$ is an alkyl group having 1 to 5 carbon atoms, said hair also being subjected to treatment with an anionic conditioning agent.

7. The process according to claim 3 wherein the short chain primary intermediate has the formula:

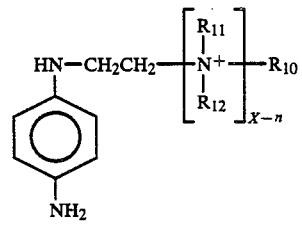

wherein $R_{11}$ and $R_{12}$ are methyl or ethyl, $R_{10}$ is alkyl containing 1 to 4 carbon atoms, and $X^{-n}$ is an anion, wherein n=1, 2, or 3.

8. The process according to claim 1 wherein said composition contains a coupler having the formula:

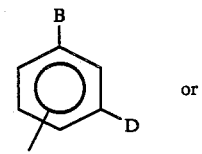

or

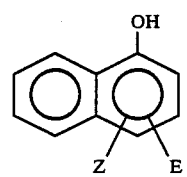

wherein
B is $NHR_{13}$, OH or $NH_2$,
D is $NHR_{13}$, OH or $NH_2$
Z is H, $R_{14}$, or $NHR_{13}$, and
E is H, $NH_2$, $R_{13}$, or $NHR_{14}$
in which
$R_{13}$ is selected from the group consisting of long chain alkyl groups having 7 to 32 carbon atoms and the radical

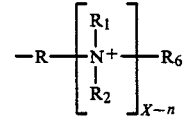

in which R, $R_1$, $R_2$, $R_6$ and $X^{-n}$, have the same meanings ascribed to them in claim 1; $R_{14}$ is a long chain alkyl group having 7 to 32 carbon atoms; and in which at least one of B, D, E or Z is the radical $NHR_{13}$ or $R_{14}$.

9. The process according to claim 1 wherein said composition contains, in addition to a modified primary intermediate, a conventional primary intermediate and a conventional coupler, said conventional coupler being present in said composition in sufficient quantity to react with said modified primary intermediate to color and/or condition said hair and to react with said conventional primary intermediate to color said hair.

10. A process according to claim 1 wherein said primary intermediate and/or said coupler contains a long chain aliphatic hydrophobic group.

* * * * *